United States Patent [19]

Olah

[11] Patent Number: 4,503,263

[45] Date of Patent: Mar. 5, 1985

[54] PROCESS FOR THE PREPARATION OF OCTANE BOOSTING BRANCHED ALIPHATIC ETHERS USING SOLID SUPERACID CATALYSTS

[75] Inventor: George A. Olah, Beverly Hills, Calif.

[73] Assignee: Atochem, Paris la Defense, France

[21] Appl. No.: 414,434

[22] Filed: Sep. 2, 1982

Related U.S. Application Data

[63] Continuation of Ser. No. 178,890, Aug. 18, 1980, abandoned.

[51] Int. Cl.$^3$ .............................................. C07C 41/05
[52] U.S. Cl. .................................... 568/694; 568/697; 568/698; 208/17
[58] Field of Search ........................ 568/697, 698, 694

[56] References Cited

U.S. PATENT DOCUMENTS

| | | | |
|---|---|---|---|
| 2,067,385 | 1/1937 | Evans et al. | 568/697 X |
| 2,732,398 | 1/1956 | Brice et al. | 260/513 F X |
| 2,805,261 | 9/1957 | Keith | 568/694 |
| 3,917,721 | 11/1975 | Frampton | 568/694 X |
| 4,080,391 | 3/1978 | Tsumura et al. | 568/694 X |
| 4,182,914 | 1/1980 | Imaizumi | 568/697 |
| 4,187,384 | 2/1980 | Platz et al. | 568/697 X |

FOREIGN PATENT DOCUMENTS

| | | |
|---|---|---|
| 2481694 | 6/1981 | France . |
| 2075019 | 11/1981 | United Kingdom . |

OTHER PUBLICATIONS

Evans et al., Ind. & Eng. Chemistry, (1936), vol. 28, No. 10, pp. 1186–1188.

*Primary Examiner*—Bernard Helfin
*Attorney, Agent, or Firm*—Pennie & Edmonds

[57] ABSTRACT

The invention concerns a process for the preparation of aliphatic ethers by reacting the corresponding alcohol and/or olefin over a superacid catalyst.

12 Claims, No Drawings

PROCESS FOR THE PREPARATION OF OCTANE BOOSTING BRANCHED ALIPHATIC ETHERS USING SOLID SUPERACID CATALYSTS

This is a continuation of application Ser. No. 178,890, filed Aug. 18, 1980, and now abandoned.

FIELD OF THE INVENTION

The invention relates to a process for the preparation of aliphatic ethers by reacting the corresponding alcohol and/or olefin over a superacid catalyst.

BACKGROUND OF THE INVENTION

Gasoline additives, such as methyl tert-butyl ether (MTBE) gained significance in recent years. They help to boost octane ratings of gasoline within the use of organometallic or other environmentally unacceptable additives such as carcinogenic aromatics.

Standard methods for the preparation of ethers include dehydration of alcohols (with sulfuric acid or other acid catalysts, such as p-toluenesulfonic acid) reaction of sodium or potassium alcoholates with alkyl (aryl) halides (the so-called Williamson synthesis), or in the case of reactive halides (such as triphenylmethyl chloride), their reaction with alcohols in the presence of pyridine or other bases.

SUMMARY OF THE INVENTION

The present invention relates to the discovery of an efficient new process for the preparation of aliphatic ethers, particularly those containing branched chains, as well as mixtures thereof, suitable as gasoline additives providing significantly increased octane ratings.

The process involves the reaction of alcohols alone or in admixture with different alcohols and/or with an olefin over a superacid catalyst to obtain the corresponding ethers or mixed ethers. The invention further includes the reaction of an olefin and water over a superacid catalyst to obtain the corresponding ether.

DETAILED DESCRIPTION OF THE INVENTION

In the case of preparing symmetrical ethers, the reaction of the corresponding alcohol is carried out over a solid superacidic catalyst, including $C_{10}$ to $C_{18}$ perfluorinated alkanesulfonic acids, such as perfluorodecanesulfonic acid or perfluorododecanesulfonic acid, polymeric perfluorinated sulfonic acids, such as polymeric trifluoroethylenesulfonic acid, the copolymer of tetrafluoroethylene and trifluoroethylenesulfonic acid or the acid form of commercially available DuPont Nafion resins, the copolymers of perfluorinated ethers and perfluoroalkenesulfonic acids. The process can be carried out batch-wise or in a continuous operation removing ether and water formed in the reaction. By reacting, over the same catalyst, the corresponding alcohols together with olefins, mixed ethers are obtained. The process is exemplified in examples describing the preparation of diisopropyl ether or isopropyl tert-butyl ether.

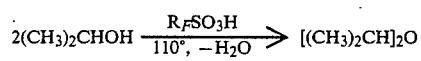

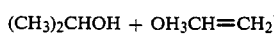

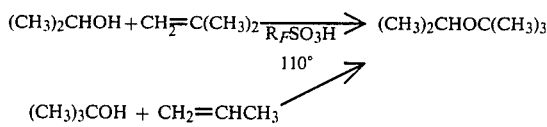

When carrying out the latter reaction with tert-butyl alcohol and propylene, a single ether is obtained, whereas reacting isopropyl alcohol with isobutylene, besides the mixed isopropyl tert-butyl ether, diisopropyl ether, the dehydration product of isopropyl alcohol is formed as the predominant product. When reacting together tert-butyl alcohol and isopropyl alcohol a mixture of tert-butyl isopropyl ether and diisopropyl ether is obtained, but no di-tert-butyl ether. As both ethers have high octane numbers, but differ in their boiling points (see Table) the use of mixtures of ethers can be also advantageous. On the other hand, as shown in preparation from tertiary alcohols, the reaction with olefins can be directed to give single products. Further, propylene and isobutylene also form low molecular weight oligomers (dimers, trimers, tetramers) as by-products, which, however, due to their branched nature may be advantageous in mixtures to be used as gasoline additives.

The temperature of the process can also be used to control product compositions. Methyl alcohol and isobutylene at 90° C. gives 95% yield of methyl tert-butyl ether (MTBE).

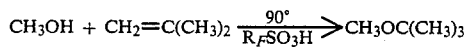

In contrast when reacting at higher temperatures, such as 170°–200°, dimethyl ether is formed preferentially.

Ethyl tert-butyl ether is similarly obtained in nearly quantitative yield from tert-butyl alcohol and ethylene.

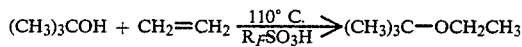

and is also obtained from ethyl alcohol and isobutylene.

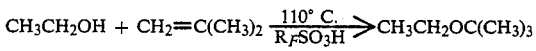

As ethyl alcohol is of increasing significance as a motor fuel, ethyl tert-butyl ether is of significance as an additive readily obtainable from the alcohol and isobutylene.

| Comparison of the Boiling Range of Gasoline Additive Branched Alkyl Ethers | |
|---|---|
| | bp° C. |
| $CH_3OC(CH_3)_3$ | 53–56 |
| $CH_3CH_2OC(CH_3)_3$ | 73 |
| $CH_3CH_2OCH(CH_3)_2$ | 63–64 |
| $[(CH_3)_2CH]_2O$ | 68–69 |

| Comparison of the Boiling Range of Gasoline Additive Branched Alkyl Ethers | |
|---|---|
| | bp° C. |
| $CH_3OC(CH_3)_2CH_2CH_3$ | 86 |
| $(CH_3)_3COCH(CH_3)_2$ | 91–94 |

A further significant aspect of the present invention relates to the discovery, that over the superacidic solid catalysts, it is possible to react olefins with a limited amount of water (between about 0.5 and 1.0 equivalent) to give branched chain ethers directly. An example is the preparation of diisopropyl ether in 50% yield and 95% selectivity from propylene, the balance being isopropyl alcohol.

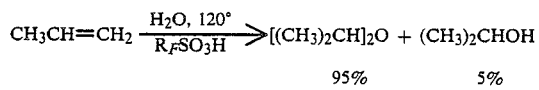

$$CH_3CH{=}CH_2 \xrightarrow[R_FSO_3H]{H_2O,\ 120°} [(CH_3)_2CH]_2O + (CH_3)_2CHOH$$
$$\phantom{CH_3CH{=}CH_2 \xrightarrow[R_FSO_3H]{H_2O,\ 120°}} 95\% \qquad 5\%$$

The invention is applicable to the reaction of olefins and alcohols in general but is particularly applicable to the lower olefins and alcohols containing up to about six carbon atoms.

The perfluorinated alkanesulfonic acids can be prepared by known methods, such as by the use of electrofluorination in preparation of perfluorinated alkanesulfonyl fluorides, which can be hydrolyzed to alkanesulfonic acids, according to the J. Chem. Soc. (London) (1947) pages 2640–2645, or by the reaction of perfluorinated alkyl iodides ($R_FI$) through their Grignard reaction with sulfur dioxide or addition of sulfonyl halides to perfluorinated olefins.

Trifluoroethylenesulfonic acid polymers can be prepared by known methods, including the hydrolysis with water and a strong base of trifluoroethylenesulfonyl fluoride polymers, according to U.S. Pat. No. 3,041,317. The hydrolysis results in the formation of the alkali salts of the polymeric sulfonic acid, from which the active acid form is liberated by treatment with $HNO_3$ or $H_2SO_4$. Tetrafluoroethylene-trifluoroethylenesulfonic acid copolymers can be similarly prepared according to Brit. Pat. No. 1,184,321.

Commercial DuPont Nafion brand ion membrane resins, such as Nafion 501 are perfluorinated polymers having sulfonic acid groups in the amount of about 0.01 to 5 mequiv/gram catalyst. The polymer is the potassium salt. Such polymers can be prepared as disclosed in Conolly et al. U.S. Pat. No. 3,282,875 and Cavanaugh et al. U.S. Pat. No. 3,882,093 by polymerizing perfluorinated vinyl compounds, or by copolymerizing the corresponding perfluorinated vinyl ethers with perfluoroethylene and/or perfluoro-alpha-olefins (U.S. Pat. No. 4,041,090). The commercial Nafion resins can be converted into their acid form by repeated treatment with aqueous strong acids, such as nitric or sulfonic acid.

A superacid is an acid having an $H_O$ value on the Hammett scale in excess of $-11$, such as $-25$. Thus weaker acids such as sulfuric acid ($H_O$ of $-11$) and HF ($H_O$ of $-10$) are excluded.

The branched chain aliphatic ethers obtainable by the described new processes disclosed in this invention, are of significant practical use as efficient and inexpensive additives to gasoline, or alcohol fuels providing significant increase of octane number.

The scope of the invention is further described in connection with the following examples, which are set forth for the purpose of illustration and are not to be considered to limit the scope of the invention in any manner.

EXAMPLE 1

10 g of perfluorododecanesulfonic acid, $C_{12}F_{25}SO_3H$ was deposited onto 90 g of porous alumina. 20 g of this catalyst was charged into a glass tube reactor of 180 mm $\times$ 10 mm dimension and 20 g/hr isopropyl alcohol was reacted over the catalyst at 110° C. A 21% conversion to diisopropyl ether with 90% selectivity was obtained.

EXAMPLE 2

50 g of commercial Nafion-K resin (potassium salt of the DuPont Company's ion-membrane material) was refluxed in 250 ml of deionized water for two hours. After filtering, the resin was treated with 100 ml of 20% to 25% nitric acid for 5 hours at room temperature. Filtering was followed by a three times repeat of the nitric acid treatment. Finally, the resin (Nafion-H) was washed to neutrality with deionized water and dried in a vacuum drying over at 105° C. for 24 hours.

15 g of the above activated Nafion-H catalyst was reacted with 20 grams/hr of isopropyl alcohol under the conditions of Example 1 giving diisopropyl ether with 26% conversion and 92% selectivity.

EXAMPLE 3

A reaction was carried out as described in Example 2 but reacting a mixture of 15 g/hr of tert-butyl alcohol and 8 g/hr propylene at 110°. A 16% conversion to tert-butyl isopropyl ether was obtained.

EXAMPLE 4

A reaction was carried out as described in Example 1, but with a mixture of 16 g/hr of methyl alcohol and 20 g/hr isobutylene at 90°. Methyl tert-butyl ether was obtained with 62% conversion and 81% selectivity.

EXAMPLE 5

A reaction was carried out as in Example 4, but in a batch-wise fashion in a stainless steel pressure autoclave with a reaction time of 2 hours. 95% conversion to methyl tert-butyl ether was obtained with 90% selectivity.

EXAMPLE 6

10 g of perfluorodecanesulfonic acid, $C_{10}F_{21}SO_3H$ was deposited on 75 g of porous chromosorb. 10 g of this catalyst was charged into a stainless steel reactor together with 21 g (0.15 mol) propylene and 4.5 g water and reacted at 120° C. for 24 hours. A 42% conversion to diisopropyl ether was obtained with 91% selectivity.

EXAMPLE 7

A reaction was carried out as under Example 6, but with the use of Nafion-H catalyst. A 50% conversion to diisopropyl ether with 95% selectivity was obtained.

EXAMPLE 8

A fixed bed stainless steel catalytic tube reactor of 150 $\times$ 10 mm dimension was charged with 10 g of polymeric trifluoroethylenesulfonic acid catalyst. Propylene 10 g/hr and water 2 g/hr were passed over the catalyst at 500 psig and 100° C. Diisopropyl ether was obtained with 16% propylene conversion and 81% selectivity.

EXAMPLE 9

A reaction was carried out as in Example 8, but using tetrafluoroethylene-trifluoroethylenesulfonic acid polymer as the catalyst. Diisopropyl ether was obtained with 13% propylene conversion and 80% selectivity.

While the invention has been described in connection with preferred embodiments, it is not intended to limit the invention to the particular forms set forth, but, on the contrary, it is intended to cover such alternatives, modifications, and equivalents as may be apparent to those skilled in the art.

I claim:

1. A process for producing branched chain aliphatic ethers which comprises passing an olefin and water in the gas phase over a solid heterogeneous $C_{10}$ to $C_{18}$ perfluorinated alkanesulfonic acid superacidic catalyst under continuous flow conditions at a reaction temperature sufficient to maintain the olefin and the water in the gas phase but below about 120° C. and contacting the olefin and the water with the catalyst for a sufficient length of time to produce an ether selectivity equal to or more than about 80%.

2. The process of claim 1 in which the amount of water is between about 0.5 and 1 equivalents.

3. The process of claim 2 in which the olefin is a lower olefin.

4. A process for producing branched chain aliphatic ethers which comprises passing an alcohol corresponding to the desired ether in the gas phase over a solid heterogeneous $C_{10}$ to $C_{18}$ perfluorinated alkanesulfonic acid superacidic catalyst under continuous flow conditions at a reaction temperature sufficient to maintain the alcohol in the gas phase but below about 120° C. and contacting the alcohol with the catalyst for a sufficient length of time to produce an ether selectivity equal to or more than about 80%.

5. The process of claim 4 in which an olefin is reacted over the catalyst together with the alcohol.

6. The process of claim 4 in which the alcohol is a lower alcohol.

7. The process of claim 5 in which the olefin is a lower olefin.

8. The process of claim 7 in which the solid heterogeneous supported perfluoroalkanesulfonic acid is supported on alumina or chromia.

9. The process of claim 3 in which the solid heterogeneous supported perfluoroalkanesulfonic acid is supported on alumina or chromia.

10. A process for the preparation of a symmetrical branched chain aliphatic ether from an alcohol containing up to six carbon atoms which comprises:
    (a) contacting said alcohol with a solid $C_{10}$ to $C_{18}$ perfluorinated alkanesulfonic acid superacidic catalyst, said catalyst being supported on alumina or chromia, at a reaction temperature sufficient to maintain the alcohol in the gaseous phase but below about 120° C.;
    (b) maintaining said contact of said alcohol with said catalyst for a sufficient time to produce said ether at a selectivity of about 80% or more;
    (c) removing said ether and any water formed by the reaction; and
    (d) recovering said symmetrical branched chain aliphatic ether.

11. A process for the preparation of a symmetrical branched chain aliphatic ether from an olefin having up to six carbon atoms which comprises:
    (a) contacting said olefin and water with a solid $C_{10}$ to $C_{18}$ perfluorinated alkanesulfonic acid superacidic catalyst, said catalyst being supported on alumina or chromia, at a reaction temperature sufficient to maintain said olefin and water in a gaseous phase but below about 120° C.;
    (b) maintaining said contact of said olefin and water with said catalyst for a sufficient time to produce said ether at a selectivity of about 80% or more; and
    (c) recovering said symmetrical branched chain aliphatic ether.

12. A process for the preparation of mixed branched chain aliphatic ethers which comprises:
    (a) reacting an alcohol having up to six carbon atoms with an olefin having up to six carbon atoms in the presence of a solid $C_{10}$ to $C_{18}$ perfluorinated alkanesulfonic acid superacidic catalyst, said catalyst being supported on alumina or chromia, at a reaction temperature sufficient to maintain the reactants in a gaseous phase but below about 120° C.;
    (b) maintaining said reaction for a sufficient time to produce said ethers at a selectivity of about 80% or more, and
    (c) recovering said mixed branched aliphatic ethers.

* * * * *

UNITED STATES PATENT AND TRADEMARK OFFICE
CERTIFICATE OF CORRECTION

PATENT NO. : 4,503,263

DATED : March 5, 1985

INVENTOR(S) : George A. Olah

It is certified that error appears in the above-identified patent and that said Letters Patent is hereby corrected as shown below:

Column 5, line 47, delete "supported" and insert --catalyst-- after "acid".

Column 6, line 2, delete "supported" and insert --catalyst-- after "acid".

Signed and Sealed this

First Day of July 1986

[SEAL]

Attest:

DONALD J. QUIGG

Attesting Officer

Commissioner of Patents and Trademarks